United States Patent [19]

Yanagi et al.

[11] Patent Number: 4,728,667
[45] Date of Patent: Mar. 1, 1988

[54] HAIR TREATMENT COMPOSITION FOR PREVENTION OF DANDRUFF IN HAIR

[75] Inventors: Mitsuo Yanagi, Machida; Masataka Ogawa, Yokohama; Uhei Tamura, Fujisawa; Tetsuo Sakamoto, Tama, all of Japan

[73] Assignee: Shiseido Company Ltd., Tokyo, Japan

[21] Appl. No.: 858,471

[22] Filed: Apr. 30, 1986

Related U.S. Application Data

[63] Continuation of Ser. No. 684,569, Dec. 21, 1984, abandoned.

[51] Int. Cl.$^4$ .................... A61K 31/355; A61K 31/17
[52] U.S. Cl. .................... 514/458; 514/596; 514/852; 514/880; 514/881; 424/DIG. 4
[58] Field of Search ................ 424/DIG. 4; 514/880, 514/881, 852, 458, 596

[56] References Cited

U.S. PATENT DOCUMENTS

| | | | |
|---|---|---|---|
| 3,846,326 | 11/1974 | Wright et al. | 514/546 |
| 4,016,287 | 4/1977 | Eberhardt et al. | 514/617 |
| 4,021,574 | 5/1977 | Bollog et al. | 514/622 |
| 4,151,269 | 4/1979 | Torii et al. | 424/70 |

FOREIGN PATENT DOCUMENTS 59-16816  1/1984  Japan .................................. 424/384

OTHER PUBLICATIONS

*Merck Index,* 9th ed., Abst. #9333 (1976).
Chem. Abst. 101:116581y.
Parran et al., *J. of Investigative Dermatology,* pp. 89–92 (1965).
Shiseido, Chem. Abst. 100:126725s.
Shiseido, Chem. Abst. 98:204435d.
Lion Fat, Chem. Abst. 90:192384f.

*Primary Examiner*—Albert T. Meyers
*Assistant Examiner*—F. Krosnick
*Attorney, Agent, or Firm*—Sprung Horn Kramer & Woods

[57] ABSTRACT

A hair treatment composition comprising 0.1% by weight or more of 3,4,4'-trichlorocarbanilide and 0.03% by weight or more of vitamine E acetate in an aqueous medium.

This hair treatment composition can effectively prevent dandruff in the hair without causing adverse side effects to the skin or scalp.

2 Claims, No Drawings

HAIR TREATMENT COMPOSITION FOR PREVENTION OF DANDRUFF IN HAIR

This is a continuation of of application Ser. No. 684,569 filed Dec. 21, 1984, now abandoned.

BACKGROUND OF THE INVENTION

1. Field of the Invention

The present invention relates to a hair treatment composition suitable for use in preventing dandruff (or scurf) in the hair. More specifically, it relates to a hair treatment composition suitable for use in preventing dandruff in the hair containing, as effective or active ingredients, trichlorocarbanilide (or triclocarban) and vitamin E acetate (i.e., the acetic acid ester of vitamin E).

2. Description of the Related Art

It is generally believed that dandruff is composed of, for example, secretions from the sebaceous glands, secretions of the sweat glands, and the scalings of the cuticle layers, and that dandruff is profused by excess secreations of, for example, the sebaceous glands. It is further believed that, when the skin or scalp is infected with bacteria or yeasts, dandruff is abnormally accelerated. For this reason, hair treatment compositions containing bacteriocides have been heretofore used for preventing dandruff in the hair. For example, it is well-known in the art that zinc pyrithione (i.e., "ZPT" hereinbelow) when used in the hair treatment composition is the most effective agent for preventing dandruff in the hair.

However, some bacteriocides have adverse side effects and, therefore, it is desirable to avoid the use of a relatively large amount of bactericides in hair treatment compositions.

SUMMARY OF THE INVENTION

Accordingly, the objects of the present invention are to eliminate the above-mentioned problems and to provide a hair treatment composition having no adverse side effects on the skin or scalp and capable of effectively preventing dandruff in the hair.

Other objects and advantages of the present invention will be apparent from the description set forth hereinbelow.

In accordance with the present invention, there is provided a hair treatment composition comprising 0.1% by weight or more of 3,4,4'-trichlorocarbanilide (i.e., "TCC" hereinbelow) and 0.03% by weight or more of vitamin E acetate (i.e., "VEA" hereinbelow) in an aqueous medium.

DESCRIPTION OF THE PREFERRED EMBODIMENTS

According to the present invention, dandruff is effectively prevented by the use of the hair treatment composition containing, as effective or active ingredients, TCC and VEA. Although it is not clearly understood how dandruff in the hair can be prevented by the hair treatment composition according to the present invention, it is believed, without prejudice to the present invention, that the metabolic reaction in the scalp is adequately or moderately adjusted to prevent dandruff in the hair. It has been found that the effect of the combined use of TCC and VEA on the prevention of dandruff in the hair is far superior to that of the sole use of TCC or VEA and is also superior to that of the use of conventional ZPT.

The TCC usable as one of the active ingredients in the hair treatment composition is 3,4,4'-trichlorocarbanilide, which is commercially available in the name of TCC. TCC is generally produced in the form of a white powder and is generally soluble in organic solvents such as acetone, dimethylformamide, methylisobutylketone, and dioxane and certain polyols such as polyethylene glycol, dipropylene glycol, and butylene glycol. However, TCC is insoluble or only slightly soluble in water and alcohols (e.g., ethanol). TCC can be readily formulated into hair treatment compositions in any conventional manner already used for formulation powdery substances into cosmetic compositions. For example, TCC can be dispersed in an aqueous or oily medium by a conventional agitating means.

VEA usable as the other active ingredient in the hair treatment composition is a viscous amorphous oily substance, and is soluble in, for example, fats and fatty oils, paraffins, and organic solvents such as acetone, methanol, ethanol, and chloroform. However, VEA is insoluble or only slightly soluble in water or aqueous organic solvents. VEA can be formulated in any conventional manner already used for formulating oily substances into cosmetic compositions.

A too small amount of TCC or VEA contained in the hair treatment composition is not effective for preventing dandruff in the hair. Accordingly, the hair treatment composition according to the present invention should contain 0.1% by weight or more, preferably 0.1% to 1% by weight, of TCC and 0.03% by weight or more, preferably 0.03% to 3% by weight, of VEA in an aqueous medium.

When TCC alone is formulated in an amount of 3% by weight or more, preferably 5% by weight or more, into a hair treatment composition, the desired prevention of dandruff in the hair can be obtained. However, when a too large amount of TCC is formulated into a hair treatment composition, adverse side effects are likely to occur together with stability problems in the dispersion or solution systems. For this reason, the use of a large amount of TCC in the hair treatment composition should be avoided.

Furthermore, when VEA alone is formulated in an amount of 1% by weight or more into a hair treatment composition, the resultant hair treatment composition can prevent dandruff in the hair. However, when VEA is used in combination with 0.1% by weight of TCC in a hair treatment composition, only a very small amount (i.e., 0.03% by weight or more) of VEA is sufficient to provide a dandruff preventing effect superior to or comparable to that of ZPT conventionally used in hair treatment compositions.

The term "a hair treatment composition" used herein includes any cosmetic composition capable of being applied to the hair or scalp. Examples of such cosmetic compositions are hair tonics, hair liquids, liquid creams for scalp treatment, hair creams, hair shampoos, hair rinses, hair conditioners, hairdressing, and hair sprays.

The hair treatment composition according to the present invention can be prepared by including the above-mentioned amounts of TCC and VEA in any aqueous medium in any conventional manner. The aqueous medium can optionally contain any conventional optional ingredients used in cosmetic treatments. Examples of such optional ingredients are 1% to 75% by weight of alcohols such as ethanol, 0.1% to 50% by weight of oily components such as octyldodecanol, mineral oil, silicone oil, fatty alcohols, and squalane, 0.01% to 70% by weight of surfactants such as polyoxyethylene hydrogenated castor oil, polysorbates, lauryl ether sulfates cocoamphoglicinates, and coconut fatty acid diethanolamide 0.1% to 30% by weight of humectant such as glycerin, propylene glycol, polyethylene glycol, dipropylene glycol, and butylene glycol, 0.01% to 5% by weight of thickening agents such as methylcellulose, hydroxyethylcellulose, carboxyvinylpolymer, magnesium aluminum silicate, and xantham gum, 0.001% to 0.5% by weight of preservatives such as parabenes, and benzoic acid and the salts thereof, 0.05% to 0.5% by weight of ultraviolet absorbers such as 2-hydroxy-4-methoxybenzophenone, 0.00001% to 0.1% by weight of coloring agents such as dyes and pigments and 0.01% to 3% by weight of various perfumes.

EXAMPLES

The present invention will now be further illustrated by, but is by no means limited to, the following examples.

EXAMPLE 1

A 0.3% weight of TCC and 0.1% by weight of VEA were formulated into a hair shampoo. The antidandruff effect of this hair shampoo was evaluated as compared with a shampoo containing ZPT.

A 15 g amount of triethanolamine lauryl sulfate, 5 g of coconut fatty acid diethanolamide, 0.3 g of TCC, 0.1 g of VEA, and appropriate amounts of a coloring agent (i.e., FD & C yellow No. 5) and a perfume were added in that order into 79.6 g of purified water (i.e., deionized water). The mixture was heated to a temperature of 70° C. for 30 minutes, while stirring, and the resultant mixture was cooled to a room temperature. Thus, a hair shampoo composition I was obtained.

As a control, a commercially available hair shampoo composition II containing 1% by weight of ZPT was used.

The effects of the hair shampoo compositions I and II on the prevention of dandruff were evaluated by using a test panel comprising 6 males aged 22 to 36 having a scalp condition wherein a relatively large amount of dandruff is profused.

A sample of each of the hair shampoo compositions I and II was applied to 3 males.

The test was carried out as follows. That is, the hair was washed with a conventional shampoo before the start of the test. The dandruff accumulated for three days after the shampooing was collected and weighed. Furthermore, the hair was washed with the above-mentioned hair shampoo composition I or II once every three days for one month and, thereafter, the dandruff accumulated for three days after the final shampooing during the test period was weighed. The collection of the accumulated dandruff was carried out by cleaning the head portion with a suction device provided with a cloth filter.

The results were as shown in Table 1. The dandruff reduction percentage in the case of each shampoo composition was calculated as follows:

Reduction (%) =

$$\frac{\left(\begin{array}{c}\text{Amount of dandruff}\\\text{before test}\end{array}\right) - \left(\begin{array}{c}\text{Amount of dandruff}\\\text{1 month after test}\end{array}\right)}{\text{Amount of dandruff before test}} \times 100$$

TABLE 1

| Sample | Panel | Amount of dandruff (mg) Before test | 1 month after test | Reduction amount (mg) | Average reduction |
|---|---|---|---|---|---|
| Shampoo I | 1 | 45.43 | 32.34 | 28.8 | |
| (TCC + | 2 | 51.68 | 25.39 | 50.9 | 36.8 |
| VEA) | 3 | 39.67 | 23.85 | 30.6 | |
| Shampoo II | 4 | 123.2 | 90.2 | 26.8 | |
| (ZPT) | 5 | 42.6 | 29.8 | 30.0 | 30.4 |
| | 6 | 33.4 | 21.9 | 34.4 | |

As is clear from the results shown in Table 1, the shampoo composition I containing TCC and VEA according to the present invention exhibited the antidandruff effects approximately comparable to or somewhat superior to that of the shampoo composition II.

The effects of the hair shampoo compositions on the prevention of dandruff were evaluated by changing the concentrations of TCC and VEA. The samples were prepared by formulating TCC and VEA in the amounts listed in Table 2 into a commercially available shampoo composition comprising containing sodium lauryl ether sulfate and coconut fatty acid diethanolamide in an aqueous medium.

TABLE 2

| Sample No. | Concentrating of TCC (% by weight) | Concentration of VEA (% by weight) |
|---|---|---|
| 1 | 5.0 | 0 |
| 2 | 0.5 | 0 |
| 3 | 0.5 | 0.1 |
| 4 | 0.3 | 0 |
| 5 | 0.3 | 0.1 |
| 6 | 0.1 | 0.05 |
| 7 | 0.1 | 0.1 |
| 8 | 0 | 0.5 |

The test was carried out by using 40 males aged 22 to 36 randomly selected and divided into 8 groups. Each sample was applied to 5 males in each group.

The shampoo sample was applied to the hair after the hair was washed once three days. The amount of dandruff accumulated for three days after the final shampooing before the test and the amount of dandruff accumulated for three days after the final shampooing during the test period was weighed. From the amounts of the accumulated dandruff thus obtained, the reduction percentage of the dandruff by the use of the shampoo composition was calculated as mentioned above. The results were evaluated as effective where the reduction percentage was not less than 10% and as ineffective where the reduction percentage was less than 10%.

The results were as shown in Table 3.

TABLE 3

| Sample No. | Effect on prevention of dandruff Effective (No. of males) | Ineffective (No. of males) |
|---|---|---|
| 1 | 4 | 1 |
| 2 | 0 | 5 |
| 3 | 4 | 1 |
| 4 | 0 | 5 |
| 5 | 5 | 0 |

TABLE 3-continued

| | Effect on prevention of dandruff | |
|---|---|---|
| Sample No. | Effective (No. of males) | Ineffective (No. of males) |
| 6 | 3 | 2 |
| 7 | 3 | 2 |
| 8 | 0 | 5 |

As is clear from the results shown in Table 3, no effect on the prevention of dandruff was exhibited for all of the five members in the case of sample No. 4 containing 0.3% by weight of TCC alone. Contrary to this, the desired effect on the prevention of dandruff was exhibited for all of the five members in the case of sample No. 5 containing both 0.3% by weight of TCC and 0.1% by weight of VEA.

Furthermore, it was observed that no effect was exhibited for all of the five members in the case of sample No. 2 containing only 0.5% by weight of TCC, whereas the desired effect was exhibited for four in five members in the case of sample No. 3 containing both 0.5% by weight of TCC and 0.1% by weight of VEA.

Contrary to above, no effect was exhibited in the case of sample No. 8 containing 0.5% by weight of VEA alone.

As is clear from the above results, the desired effect on the prevention of dandruff can be exhibited by using shampoo compositions containing 0.3% by weight or more of TCC and 0.1% by weight or more of VEA.

EXAMPLE 2

A shampoo composition having the following composition was prepared in the same manner as in Example 1.

| Ingredients | % by weight |
|---|---|
| Sodium lauryl sulfate | 5 |
| Lauryl sulfate - triethanolamine | 5 |
| Lauryl dimethylamino acetic acid betaine | 6 |
| Ethylene glycol distearate | 2 |
| Polyethylene glycol (M.W. = 400) | 5 |
| TCC | 0.3 |
| VEA | 0.1 |
| Perfume | 0.3 |
| Purified water | to 100% by weight |

The resultant shampoo composition was evaluated in the same manner as in Example 1, in comparison with a comparative shampoo composition containing neither TCC nor VEA. As a result, the desired effect on preventing dandruff was obtained for five members in the shampoo composition obtained above.

EXAMPLE 3

A shampoo composition having the following composition was prepared in the same manner as in Example 1.

| Ingredients | % by weight |
|---|---|
| Polyoxyethylene (Ave. E.O. = 3 mol) lauryl ether sulfate - Na | 10 |
| Polyoxyethylene (Ave. E.O. = 3 mol) lauryl ether sulfate - triethanolamine | 7 |
| Lauric acid diethanol amide | 4 |
| Dipropylene glycol | 5 |
| TCC | 0.3 |
| VEA | 0.1 |
| Perfume | 0.3 |
| Purified water | to 100% by weight |

The resultant shampoo composition was evaluated in the same manner as in Example 1, in comparison with a comparative shampoo composition containing neither TCC nor VEA. As a result, the desired antidandruff effects were obtained for five members in the shampoo composition obtained above.

EXAMPLE 4

A shampoo composition having the following composition was prepared in the same manner as in Example 1.

| Ingredients | % by weight |
|---|---|
| Sodium lauroyl methyl taurine | 10 |
| Lauryl dimethyl aminoacetic acid betaine | 8 |
| Lauric acid diethanol amide | 4 |
| Ethylene glycol fatty acid ester | 1.5 |
| Polyethylene glycol (M.W. = 1500) | 5 |
| TCC | 0.3 |
| VEA | 0.1 |
| Perfume | 0.3 |
| Purified water | to 100% by weight |

The resultant shampoo composition was evaluated in the same manner as in Example 1, in comparison with a comparative shampoo composition containing neither TCC nor VEA. As a result, the desired effect on preventing dandruff was obtained for five members in the shampoo composition obtained above.

EXAMPLE 5

A shampoo composition having the following composition was prepared in the same manner as in Example 1.

| Ingredients | % by weight |
|---|---|
| Sodium cocoyl methyl taurine | 10 |
| Alkyl ($C_{11}$) imidazolinium betaine | 6 |
| Coconut fatty acid diethanol amide | 4 |
| Polyoxyethylene (Ave. E.O. = 13 mol) polyoxypropylene (Ave. P.O. = 30 mol) block polymer | 3 |
| TCC | 0.3 |
| VEA | 0.1 |
| Perfume | 0.3 |
| Purified water | to 100% by weight |

The resultant shampoo composition was evaluated in the same manner as in Example 1, in comparison with a comparative shampoo composition containing neither TCC nor VEA. As a result, the desired antidandruff effects were obtained for five members in the shampoo composition obtained above.

EXAMPLE 6

A shampoo composition having the following composition was prepared in the same manner as in Example 1.

| Ingredients | % by weight |
|---|---|
| Sodium lauryl sarcosine | 10 |
| Lauryl dimethylamino acetic acid betaine | 8 |

-continued

| Ingredients | % by weight |
|---|---|
| Lauric acid diethanol amide | 4 |
| Polyoxypropylene (Ave. P.O. = 9 mol) diglyceryl ether | 5 |
| TCC | 0.3 |
| VEA | 0.1 |
| Perfume | 0.3 |
| Purified water | to 100% by weight |

The resultant shampoo composition was evaluated in the same manner as in Example 1, in comparison with a comparative shampoo composition containing neither TCC nor VEA. As a result, the desired antidandruff effects were obtained for five members in the shampoo composition obtained above.

EXAMPLES 7 TO 13

Hair rinse compositions having the compositions listed in Table 4 were prepared in the manner as described in Example 1.

The antidandruff effects of the resultant rinse compositions thus prepared were evaluated as follows.

That is, the hair was washed with a conventional shampoo composition containing neither TCC nor VEA, and then treated with the hair rinse compositions obtained above. The results were evaluated in the same manner as in Example 1.

TABLE 4

| | | | | Example No. | | | | % by weight |
|---|---|---|---|---|---|---|---|---|
| Ingredients | | 7 | 8 | 9 | 10 | 11* | 12* | 13* |
| Dipropylene glycol | | 4 | 4 | 4 | 4 | 4 | 4 | 4 |
| Stearyl trimethylammonium chloride | | 2 | 2 | 2 | 2 | 2 | 2 | 2 |
| Stearyl alcohol | | 1 | 1 | 1 | 1 | 1 | 1 | 1 |
| Polyoxyethylene (Ave. E.O. = 60 mol) hydrogenated castor oil | | 0.5 | 0.5 | 0.5 | 0.5 | 0.5 | 0.5 | 0.5 |
| Glyceryl stearate | | 0.5 | 0.5 | 0.5 | 0.5 | 0.5 | 0.5 | 0.5 |
| TCC | | 0.2 | 0.3 | 0.15 | 0.5 | 0.5 | 0 | 0.05 |
| VEA | | 0.05 | 0.1 | 0.3 | 0.04 | 0 | 0.5 | 0.01 |
| Perfume | | 0.3 | 0.3 | 0.3 | 0.3 | 0.3 | 0.3 | 0.3 |
| Purified water | | Amount to 100% by weight in total | | | | | | |
| Anti-dandruff effect (total 5 members) | Effective (No. of members) | 4 | 5 | 4 | 4 | 0 | 0 | 0 |
| | Ineffective (No. of members) | 1 | 0 | 1 | 1 | 5 | 5 | 5 |

*Comparative Examples

As is clear from the results shown in Table 4, the hair rinse compositions of Examples 7 to 10 according to the present invention exhibited the desired antidandruff effects.

EXAMPLE 14

A hair tonic composition having the following composition was prepared by first mixing the ingredients other than water, while stirring, followed by adding water thereto.

| Ingredients | % by weight |
|---|---|
| 95% ethyl alcohol | 50 |
| Polyoxyethylene (E.O. = 40 mol) hydrogenated castor oil | 0.5 |
| TCC | 0.3 |
| VEA | 0.1 |
| Perfume | 0.5 |
| Water | to 100% by weight |

The resultant hair tonic composition exhibited excellent antidandruff effects, when tested in a manner as in Example 1.

EXAMPLE 15

A hair liquid composition having the following composition was prepared in the same manner as in Example 14.

| Ingredients | % by weight |
|---|---|
| 95% ethyl alcohol | 50 |
| Polyoxypropylene (P.O. = 40 mol) butyl alcohol | 15 |
| TCC | 0.3 |
| VEA | 0.1 |
| Perfume | 0.5 |
| Purified water | to 100% by weight |

The resultant hair liquid composition exhibited excellent antidandruff effects when evaluated in a manner as in Example 1.

EXAMPLE 16

A hair cream composition having the following composition was prepared by first mixing, while stirring, the ingredients of Part (A) upon heating, and then adding the resultant mixture to the heated mixture of Part (B) followed by cooling.

| Ingredients | % by weight |
|---|---|
| Part (A) | |
| Liquid paraffin | 15 |
| Cetyl alcohol | 5 |
| Vaseline | 4 |
| Glycerine monostearate | 3 |
| Polyoxyethylene (E.O. = 20 mol) oleyl alcohol | 1 |
| TCC | 0.3 |
| VEA | 0.1 |
| Perfume | 0.5 |
| Part (B) | |
| Dipropylene glycol | 10 |
| Purified water | to 100% by weight |

The resultant O/W type hair cream composition exhibited excellent antidandruff effects, when evaluated in a manner as in Example 1.

EXAMPLE 17

A hair lotion having the following composition was prepared by mixing, while stirring, the ingredients of Part (A), and then adding the resultant mixture to the mixture of Part (B).

| Ingredients | % by weight |
| --- | --- |
| Part (A) | |
| 95% Ethyl alcohol | 40 |
| Dimethylpolysiloxane | 0.5 |
| Liquid paraffin | 0.5 |
| Polyoxyethylene (E.O. = 40 mole) hydrogenated oil | 0.5 |
| Acrylic resin alkanol amine solution | 0.5 |
| TCC | 0.3 |
| VEA | 0.1 |
| Perfume | 0.2 |
| Part (B) | |
| Dipropylene glycol | 3 |
| Purified water | to 100% by weight in total of (A) & (B) |

The resultant hair lotion obtained above exhibited excellent antidandruff effects, when evaluated in a manner as in Example 1.

EXAMPLE 18

A hair lotion having the following composition was prepared in the same manner as in Example 17.

| Ingredients | % by weight |
| --- | --- |
| Part (A) | |
| 95% Ethyl alcohol | 50 |
| Dimethyl polysiloxane | 2 |
| Liquid paraffin | 2 |
| Stearyl trimethyl ammonium chloride | 0.3 |
| TCC | 0.3 |
| VEA | 0.1 |
| Perfume | 0.2 |
| Part (B) | |
| 1,3-Propylene glycol | 5 |
| Purified water | to 100% by weight in total of (A) & (B) |

The resultant hair lotion composition obtained above exhibited excellent antidandruff effects.

We claim:

1. An aqueous anti-dandruff composition consisting essentially of 0.15% to 0.5% by weight of 3,4,4'-trichlorocarbanilide and 0.04% to 0.3% by weight of vitamin E acetate in an aqueous medium, the weight ratio of 3,4,4'-trichlorocarbanilide to the vitamin E acetate being 12.5:1 to 0.5:1.

2. A method of treating dandruff which comprises applying to the hair or scalp an anti-dandruff effective amount of a composition according to claim 1.

* * * * *